United States Patent
Berall

(12) 
(10) Patent No.: US 6,494,828 B1
(45) Date of Patent: Dec. 17, 2002

(54) LARYNGOSCOPE

(76) Inventor: Jonathan Berall, 173 Columbia Heights, Brooklyn, NY (US) 11201

( * ) Notice: Subject to any disclaimer, the term of this patent is extended or adjusted under 35 U.S.C. 154(b) by 0 days.

(21) Appl. No.: 09/910,546

(22) Filed: Jul. 23, 2001

(51) Int. Cl.[7] .................................................. A61B 1/26
(52) U.S. Cl. ........................ 600/190; 600/186; 600/194; 600/195
(58) Field of Search ........................... 600/120, 185–194

(56) References Cited

U.S. PATENT DOCUMENTS 5,063,907 A * 11/1991 Musicant et al. ............ 600/186
D399,957 S * 10/1998 Chernov et al. ............ D24/138

FOREIGN PATENT DOCUMENTS

EP 0499784 * 3/1991 ............ A61B/1/26

* cited by examiner

*Primary Examiner*—John Mulcahy
(74) *Attorney, Agent, or Firm*—Charles E. Baxley

(57) ABSTRACT

An improved laryngoscope of the type having a handle for grasping and a blade being rigid and extending from the handle for inserting into the mouth of a patient during use. The improvement includes the blade being so shaped for contacting, supporting, and displacement of the bottom of the mouth of the patient and not bearing on the lower teeth of the patient so as to avoid damage to the lower teeth of the patient during use and so as to allow the lower jaw of the patient to be opened during use and being so shaped for contacting the front of the lower jaw of the patient so as to allow the lower jaw of the patient to be thrust forwardly during use.

14 Claims, 4 Drawing Sheets

LARYNGOSCOPE

BACKGROUND OF THE INVENTION

1. Field of the Invention

The present invention relates to the class of surgery. More particularly, the present invention relates to the subclass of laryngoscopes.

2. Description of the Prior Art

In the course of providing patient care, particularly of an emergency nature, it is frequently necessary or desirable to visualize a portion of the mouth, the pharynx, and the larynx of a patient. Most commonly this is done for the purpose of inserting a tube through the glottis, a procedure called endotracheal intubation. In general, instruments known as laryngoscopes are widely known and used for endotracheal intubation.

The configuration of a typical prior art laryngoscope 10 can best be seen in FIG. 1, which is a diagrammatic side elevational view of a typical prior art laryngoscope in use, and as such, will be discussed with reference thereto.

The laryngoscope 10 includes two basic parts, a handle 12 and a blade 14. The handle 12 allows for grasping and the blade 14 is rigid and attached to, and extends from, the handle 12. The blade 14 is for inserting into the mouth 16 of a patient 18 to allow viewing of a portion of the mouth 16, the pharynx, and the larynx of the patient 18, who is in the so-called sniffer position, and depresses the tongue 20 and mandible in order to prevent the tongue 20 of the patient 18 from obstructing the view during examination.

One of the most common complaints of laryngoscopy, however, is damage to the teeth of the patient. Not only may there be cosmetic disfigurement, discomfort, and extensive restorative dentistry, but if the patient aspirates a dislodged tooth or fragment, there may be grave pulmonary complications.

A healthy tooth may be chipped, broken, or loosened, and a loose tooth may be avulsed. The incisors are most often injured and occasionally the canines are also.

Thus, there is a need for a laryngoscope that avoids damage to the teeth of a patient during use.

Numerous innovations for laryngoscopes have been provided in the prior art that will be described. Even though these innovations may be suitable for the specific individual purposes to which they address, however, they differ from the present invention in that they do not teach a laryngoscope whose blade is so shaped for being supported by, and contacting, the bottom of the mouth of the patient and not the lower teeth of the patient so as to avoid damage to the lower teeth of the patient during use and so as to allow the lower jaw of the patient to be opened during use and being so shaped for contacting the front of the lower jaw of the patient so as to allow the lower jaw of the patient to be thrust forwardly during use.

FOR EXAMPLE, U.S. Pat. No. Des. 410,286 to Tamirisa teaches the ornamental design for an intubating malleable fiberoptic laryngoscope.

ANOTHER EXAMPLE, U.S. Pat. No. Des. 413,977 to Cranton et al. teaches the ornamental design for a laryngoscope blade.

STILL ANOTHER EXAMPLE, U.S. Pat. No. 4,565,187 to Soloway teaches a laryngoscope that consists of a plastic disposable blade that has a hollow sleeve. The blade is removably attached to either a handle or adapter. The handle or adapter has a light emitting tube that enters the hollow sleeve so that a larynx can be illuminated. The handle and adapter can be adjustable so that various angle arrangements can be formed by the blade with respect to the handle.

YET ANOTHER EXAMPLE, U.S. Pat. No. 4,574,784 to Soloway teaches a laryngoscope that consists of an angle adjustable adapter connected between a handle and a blade or the handle itself being angle adjustable so that various angle arrangements can be formed by the blade with respect to the handle. The laryngoscope permits interchangeability between conventional and fiber-optic lighting systems of which the components thereof assemble to form a complete mixed system.

STILL YET ANOTHER EXAMPLE, U.S. Pat. No. 4,947,896 to Bartlett teaches a laryngoscope that has a blade and a removably attached handle, which can be fixed to the blade at a desired angle. The blade has a predetermined cross-section defining a plurality of channels, including a viewing channel and a plurality of service channels. The blade also supports twin halogen lights which project light down opposing axial sides of the blade structure. Electric wires run in the service channels between the lights and batteries received in the handle. An adjustable position suction tube is entrained in the blade in another service channel, with an adjustment actuator supported on the handle. A roughened surface is formed in a tongue contact area of the blade to enhance frictional engagement of the patient's tongue.

YET STILL ANOTHER EXAMPLE, U.S. Pat. No. 5,036,835 to Filli teaches an adjustable sliding laryngoscope including a blade portion including an adjustably attached spatula portion. The spatula is designed to be used as a tongue depressor to facilitate inspection of the pharynx and larynx or the insertion of anesthetic breathing tubes. The adjustable connection between the spatula portion and other portions of the blade portion is such that the length of the spatula may be adjusted to adjust for differing patient oral characteristics.

STILL YET ANOTHER EXAMPLE, U.S. Pat. No. 5,406,941 to Roberts teaches a laryngoscope for use in endotracheal intubation wherein the blade is adjustable between a straight surface and a curved surface.

YET STILL ANOTHER EXAMPLE, U.S. Pat. No. 5,827,178 to Berall teaches a laryngoscope, for use in intubating a patient's trachea, especially in emergency situations. The laryngoscope has a camera mounted in the vicinity of a distal end of its blade to observe the patient's trachea opening and other oral internal structures in a visual field. The camera is connected, typically via a fiberoptic cable, to a lightweight portable television screen, preferably mounted on the laryngoscope handle, for displaying the visual field to a Professional Intubator so as to enable him or her to observe continuously the trachea opening and other oral internal structures as he or she manipulates the intubating instrument. The laryngoscope with the camera and screen thereon preferably is held in one of the Professional Intubator's hands to lift and move aside the patient's tongue steadily and constantly. The other hand of the Professional Intubator then is free to manipulate the intubating instrument. Mounting the camera and the screen on the laryngoscope, which remains quite steady, provides the Professional Intubator with a continuous steady display of the trachea opening and other oral internal structures on the screen while the Professional Intubator also sees directly down the patient's mouth.

It is apparent that numerous innovations for laryngoscopes have been provided in the prior art that are adapted to be used. Furthermore, even though these innovations may be suitable for the specific individual purposes to which they address, however, they would not be suitable for the purposes of the present invention as heretofore described, since they do not teach a laryngoscope whose blade is so shaped for being supported by, and contacting, the bottom of the mouth of the patient and not the lower teeth of the patient so as to avoid damage to the lower teeth of the patient during use and so as to allow the lower jaw of the patient to be opened during use and being so shaped for contacting the front of the lower jaw of the patient so as to allow the lower jaw of the patient to be thrust forwardly during use.

SUMMARY OF THE INVENTION

ACCORDINGLY, AN OBJECT of the present invention is to provide a laryngoscope that avoids the disadvantages of the prior art.

ANOTHER OBJECT of the present invention is to provide a laryngoscope that maintains the lower jaw of the patient in an open and stable position making it easier for the physician to see the patient's epiglottic opening.

STILL ANOTHER OBJECT of the present invention is to provide a laryngoscope that improves control of the patient's tongue so that it does not obstruct the physician's view of the patient's epiglottic opening.

BRIEFLY STATED, YET ANOTHER OBJECT of the present invention is to provide an improved laryngoscope of the type having a handle for grasping and a blade extending from the handle for inserting into. the mouth of the patient. The improvement includes the blade being so shaped for contacting, supporting, and displacement of the bottom of the mouth of the patient and not bearing on the lower teeth of the patient so as to avoid damage to the lower teeth of the patient during use and so as to allow the lower jaw of the patient to be opened during use and being so shaped for contacting the front of the lower jaw of the patient so as to allow the lower jaw of the patient to be thrust forwardly during use. The blade has a first portion that extends from the handle in a concave configuration relative to, and for receiving but clearing and not being supported by, the lower teeth of the patient during use. The blade further has a second portion that extends upwardly from the first portion in a convex configuration relative to, and for contacting, the front of the lower jaw of the patient so as to allow the lower jaw of the patient to be thrust forwardly during use. The blade further has a third portion that extends outwardly from the second portion in a convex configuration relative to, and for contacting and being supported by, the bottom of the mouth of the patient so as to allow the lower jaw of the patient to be opened during use.

The novel features which are considered characteristic of the present invention are set forth in the appended claims. The invention itself, however, both as to its construction and its method of operation, together with additional objects and advantages thereof, will be best understood from the following description of the specific embodiments when read and understood in connection with the accompanying drawing.

BRIEF DESCRIPTION OF THE DRAWING

The figures of the drawing are briefly described as follows:

FIG. 4 is a diagrammatic side elevational view of the area generally enclosed by the dotted curve identified by ARROW 4 in FIG. 3 of the blade of the laryngoscope of the present invention with a first embodiment of a bearing pressure distributer thereon;

LIST OF REFERENCE NUMERALS UTILIZED IN THE DRAWING

Figure 1:
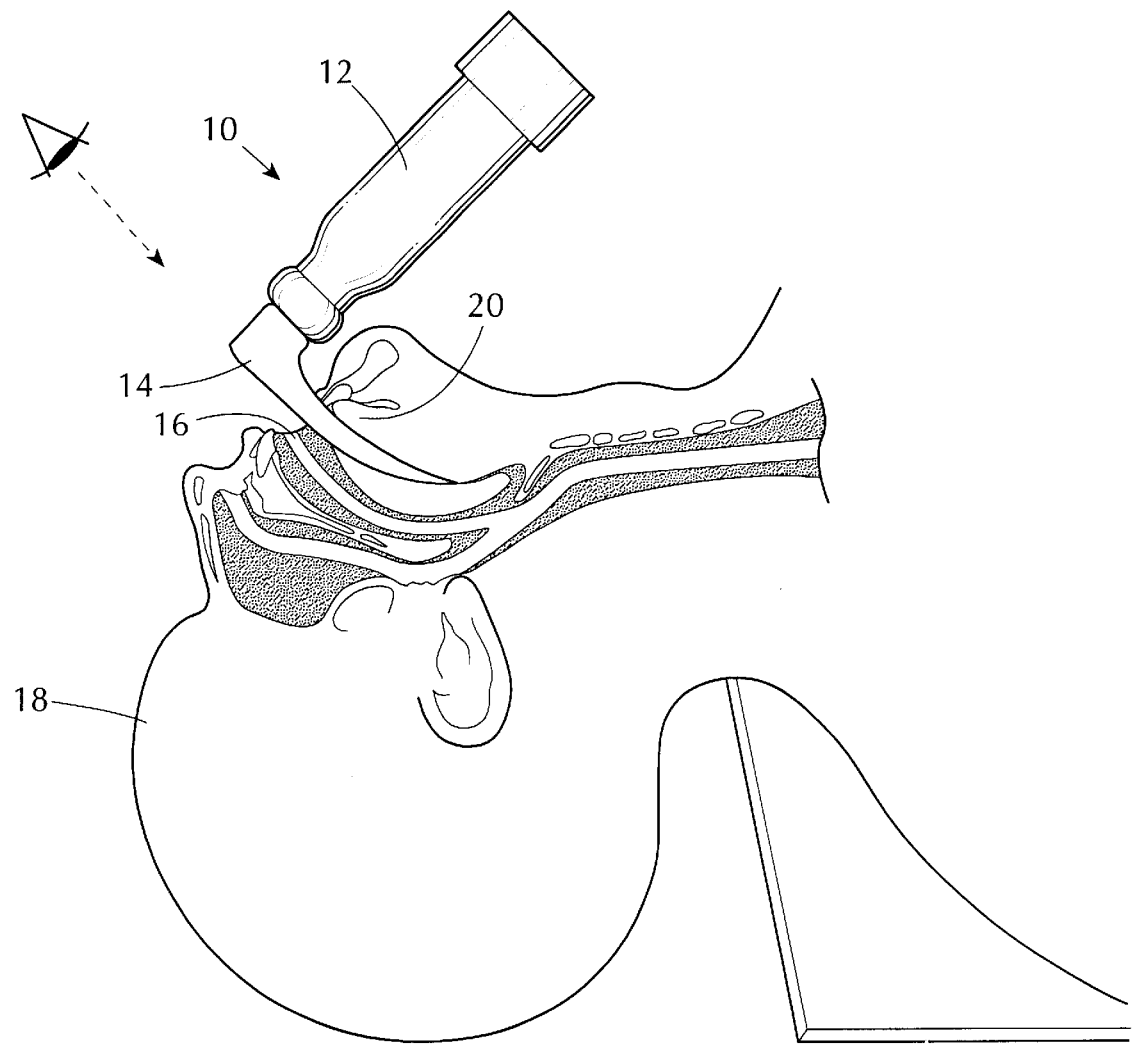
FIG. 1 is a diagrammatic side elevational view of a typical prior art laryngoscope in use.

PRIOR ART 10 laryngoscope
12 handle of laryngoscope 10 for grasping
14 blade of laryngoscope 10 for inserting into mouth 16 of patient 18 to allow viewing of portion of mouth 16, pharynx, and larynx of patient 18, who is in so-called sniffer position, and depressing tongue 20 and mandible in order to prevent tongue 20 of patient 18 from obstructing view during examination
16 mouth of patient 18
18 patient
20 tongue of patient 18

PRESENT INVENTION 15 bottom of mouth 16 of patient 18
30 improved laryngoscope of present invention
32 lower teeth of patient 18
34 front of lower jaw 36 of patient 18
36 lower jaw of patient 18
38 first portion of blade 14
40 second portion of blade 14
42 third portion of blade 14
44 proximal end of first portion 38 of blade 14
46 distal end of first portion 38 of blade 14
48 proximal end of second portion 40 of blade 14
50 distal end of second portion 40 of blade 14
52 proximal end of third portion 42 of blade 14
54 distal end of third portion 42 of blade 14 for replicating distal end of blade 14 of conventional laryngoscope 10 and for having camera 55 mounted thereon
55 camera
56 screen
58 apparatus for distributing bearing pressure of blade 14 on bottom 15 of mouth 16 of patient 18 and front 34 of lower jaw 36 of patient 18 during use
60 elasomeric lining of apparatus 58 for distributing bearing pressure of blade 14 on bottom 15 of mouth 16 of patient 18 and front 34 of lower jaw 36 of patient 18 during use
62 balloon of apparatus 58 for distributing bearing pressure of blade 14 on bottom 15 of mouth 16 of patient 18 and front 34 of lower jaw 36 of patient 18 during use 64 inflatable cushion of apparatus 58 for distributing bearing pressure of blade 14 on bottom 15 of mouth 16 of patient 18 and front 34 of lower jaw 36 of patient 18 during use

ALTERNATE EMBODIMENT 112 conventional, somewhat straight, laryngoscope blade
130 laryngoscope of present invention
138 first portion of blade
140 second portion of blade
142 third portion of blade
156 screen
166 adapter
168 one-piece unit
170 attaching apparatus
172 operating surface of conventional, somewhat straight, laryngoscope blade 112

DETAILED DESCRIPTION OF THE PREFERRED EMBODIMENT

Figure 2:
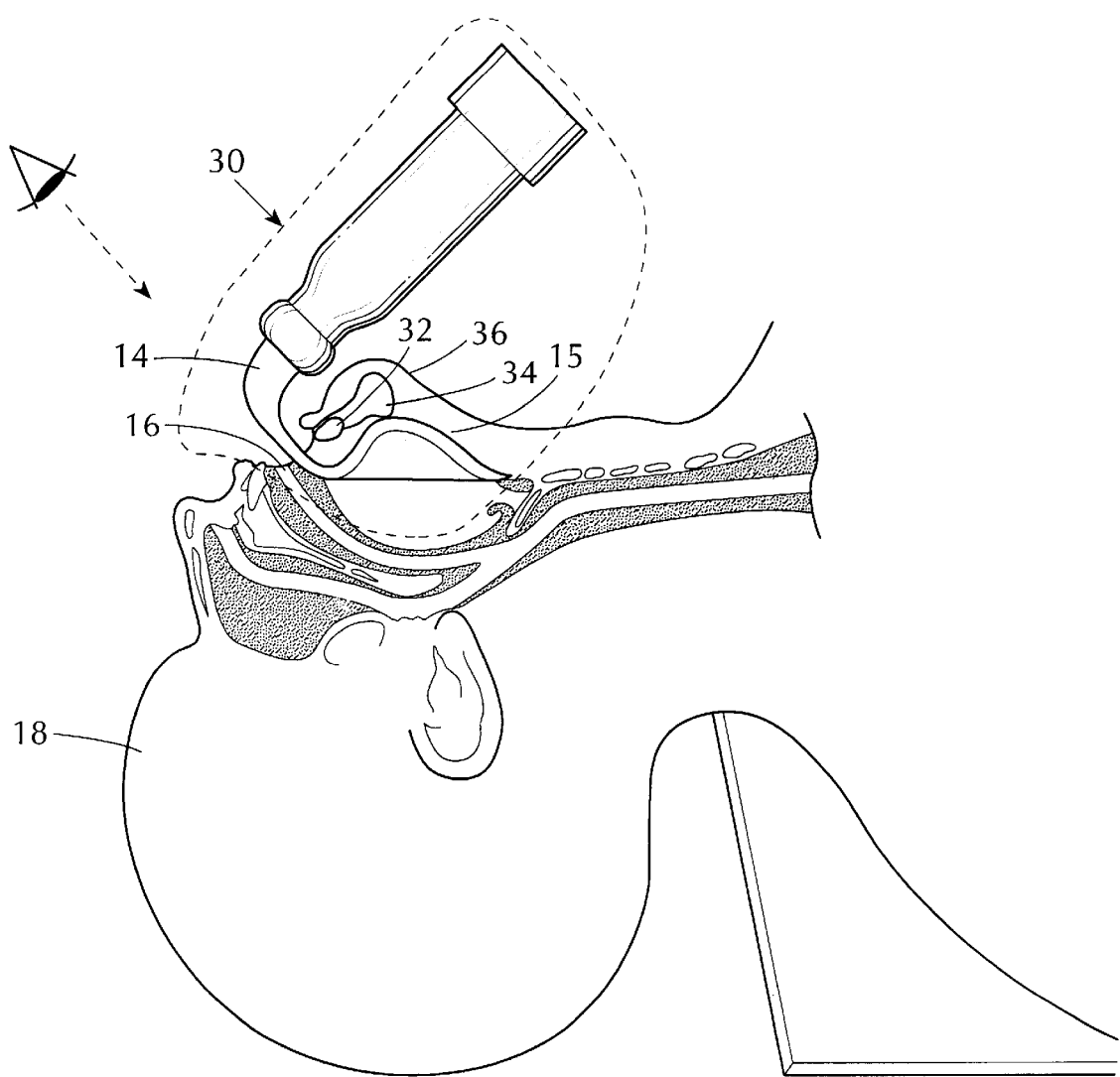
FIG. 2 is a diagrammatic side elevational view of the laryngoscope of the present invention in use.

Referring now to the figures, in which like numerals indicate like parts, and particularly to FIG. 2, which is a diagrammatic side elevational view of the laryngoscope of the present invention in use, the improved laryngoscope of the present invention is shown generally at 30.

The improved laryngoscope 30 includes the blade 14 thereof being so shaped for contacting, supporting, and displacement of the bottom 15 of the mouth 16 of the patient 18 and not bearing on the lower teeth 32 of the patient 18 so as to avoid damage to the lower teeth 32 of the patient 18 during use and so as to allow the lower jaw 36 of the patient 18 to be opened during use and being so shaped for contacting the front 34 of the lower jaw 36 of the patient 18 so as to allow the lower jaw 36 of the patient 18 to be thrust forwardly during use.

The specific configuration of the blade 14 of the improved laryngoscope 30 can best be seen in FIG. 3, which is an enlarged diagrammatic side elevational view of the area generally enclosed by the dotted curve identified by ARROW 3 in FIG. 2 of the laryngoscope of the present invention, and as such, will be discussed with reference thereto.

The blade 14 of the improved laryngoscope 30 is serpentine-shaped and includes a first portion 38, a second portion 40 that transitions smoothly upwardly from the first portion 38 thereof, and a third portion 42 that transitions smoothly outwardly from the second portion 40 thereof.

The first portion 38 of the blade 14 has a proximal end 44 that is disposed at the handle 12, and a distal end 46. The first portion 38 extends from the proximal end 44 thereof to the distal end 46 thereof in a concave configuration relative to, and for receiving but clearing and not being supported by, the lower teeth 32 of the patient 18 so as to avoid damage to the lower teeth 32 of the patient 18 during use.

The second portion 40 of the blade 14 has a proximal end that is coincident with the distal end 46 of the first portion 38 of the blade 14, and a distal end 50. The second portion 40 extends from the proximal end 48 thereof to the distal end 50 thereof in a convex configuration relative to, and for contacting, the front 34 of the lower jaw 36 of the patient 18 so as to allow the lower jaw 36 of the patient 18 to be thrust forwardly during use.

The third portion 42 of the blade 14 has a proximal end 52 that is coincident with the distal end 50 of the second portion 40 of the blade 14, and a distal end 54 for replicating the distal end of the blade 14 of the conventional laryngoscope 10 and for having a camera 55 mounted thereon. The third portion 42 extends from the proximal end 52 thereof to the distal end 54 thereof in a convex configuration relative to, and for contacting and being supported by, the bottom 15 of the mouth of the patient 18 so as to allow the lower jaw 36 of the patient 18 to be opened during use.

The first portion 38 of the blade 14 has a radius of curvature and the third portion 42 of the blade 14 has a radius of curvature that is substantially greater than the radius of curvature of the first portion 38 of the blade 14.

The improved laryngoscope 30 further includes a screen 56 that is pivotally mounted to the third portion 42 of the blade 14 and is dependable therefrom, extends conformingly to the second portion 40 of the blade 14, and is for blocking and confining the tongue 20 of the patient 18 to the side of the mouth 16 so as to prevent the tongue 20 from obstructing viewing during examination when the screen 56 is pivoted downwardly.

The improved laryngoscope 30 further includes apparatus 58 for distributing bearing pressure of the blade 14 on the bottom 15 of the mouth 16 and the front 34 of the lower jaw 36 of the patient 18 during use, and which is a resilient material.

The configuration of the apparatus 58 can best be seen in FIGS. 4–6, and as such, will be discussed with reference thereto.

Figure 3:
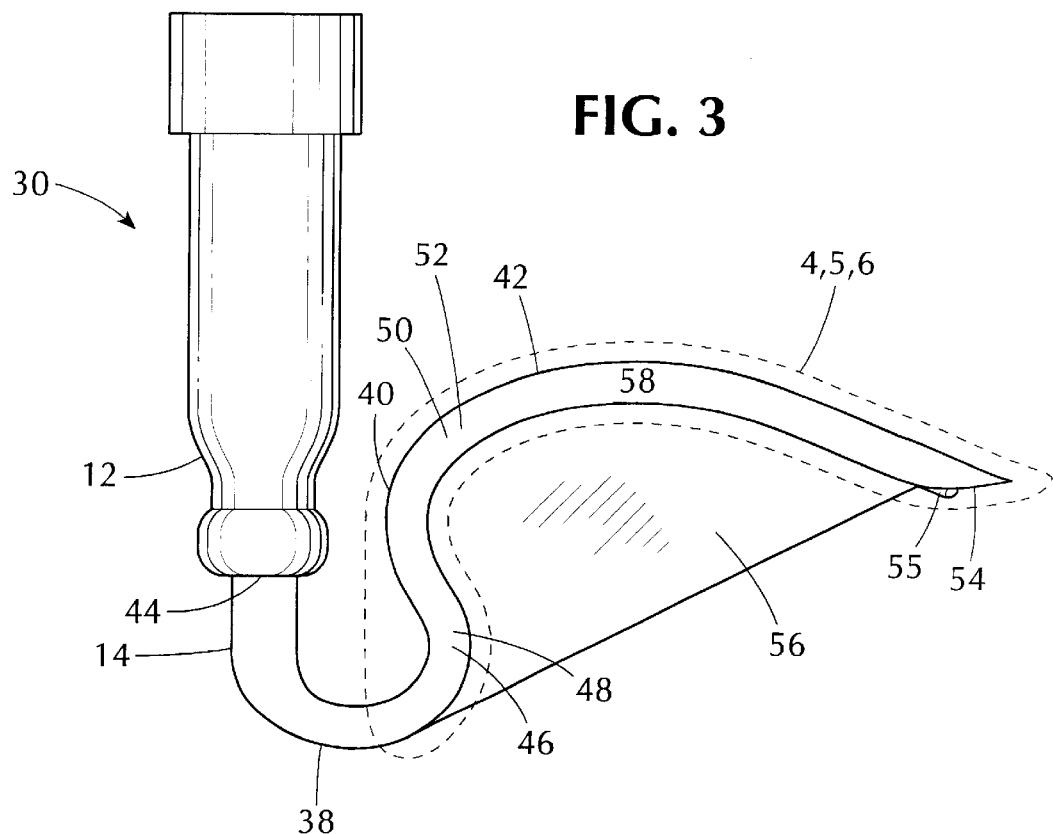
FIG. 3 is an enlarged diagrammatic side elevational view of the area generally enclosed by the dotted curve identified by ARROW 3 in FIG. 2 of the laryngoscope of the present invention.

As shown in FIG. 4, which is a diagrammatic side elevational view of the area generally enclosed by the dotted curve identified by ARROW 4 in FIG. 3 of the blade of the laryngoscope of the present invention with a first embodiment of a bearing pressure distributer thereon, a first embodiment of the apparatus 58 is an elasomeric lining 60 that extends along the blade 14.

Figure 5:
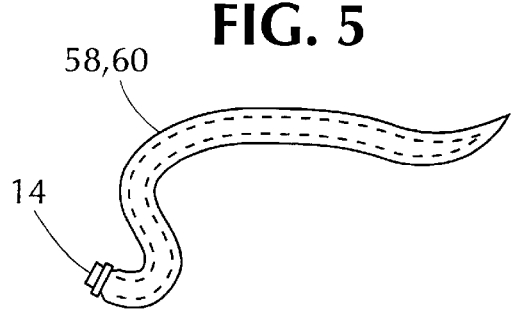
FIG. 5 is a diagrammatic side elevational view of the area generally enclosed by the dotted curve identified by ARROW 5 in FIG. 3 of the blade of the laryngoscope of the present invention with a second embodiment of a bearing pressure distributer thereon.

As shown in FIG. 5, which is a diagrammatic side elevational view of the area generally enclosed by the dotted curve identified by ARROW 5 in FIG. 3 of the blade of the laryngoscope of the present invention with a second embodiment of a bearing pressure distributer thereon, a second embodiment of the apparatus 58 is a balloon 62 that receives the blade 14.

Figure 6:
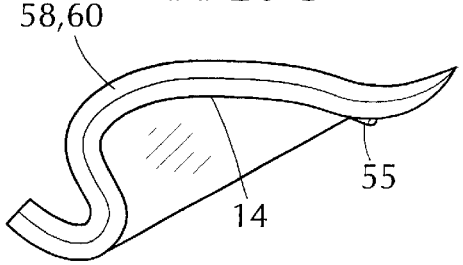
FIG. 6 is a diagrammatic side elevational view of the area generally enclosed by the dotted curve identified by ARROW 6 in FIG. 3 of the blade of the laryngoscope of the present invention with a third embodiment of a bearing pressure distributer thereon.

As shown in FIG. 6, which is a diagrammatic side elevational view of the area generally enclosed by the dotted curve identified by ARROW 6 in FIG. 3 of the blade of the laryngoscope of the present invention with a third embodiment of a bearing pressure distributer thereon, a third embodiment of the apparatus 58 is an inflatable cushion 64 that extends along the blade 14.

Figure 7:
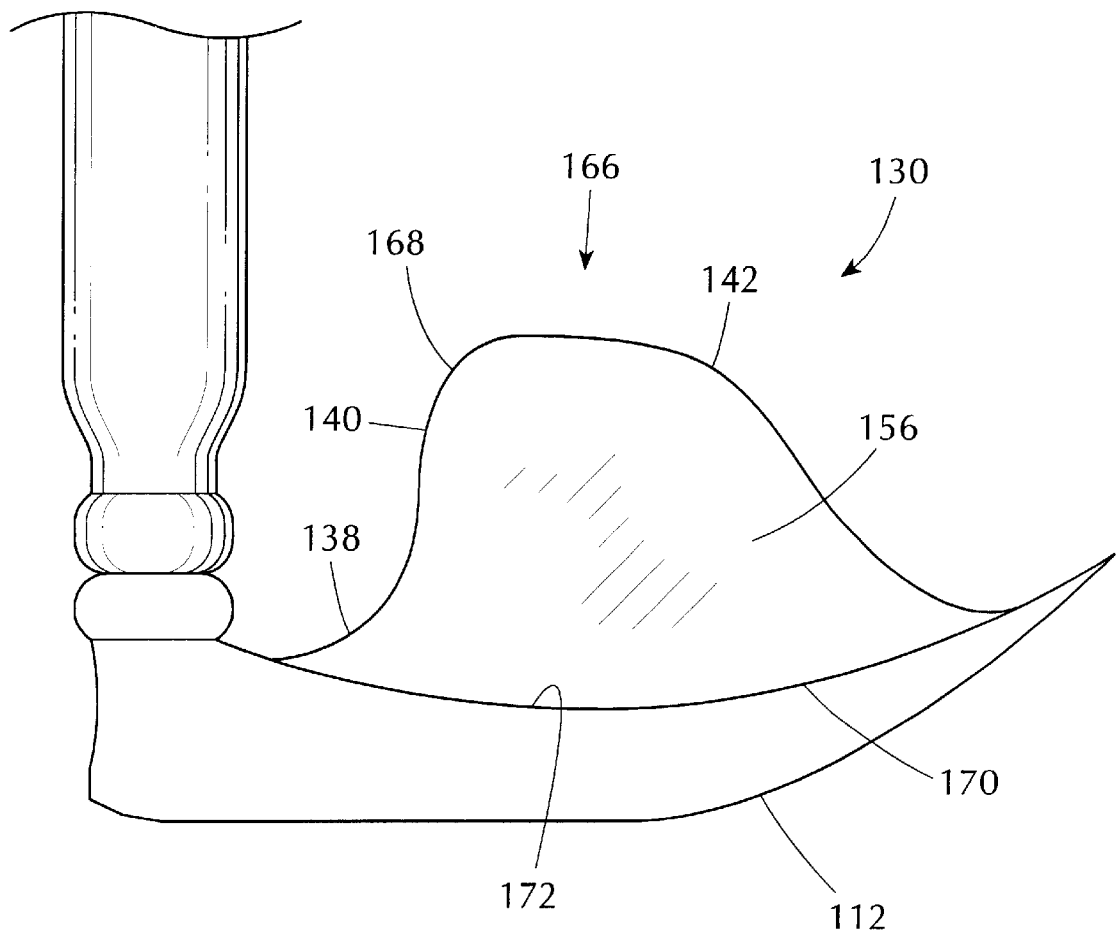
FIG. 7 is a diagrammatic side elevational view of an alternate embodiment of the present invention attached to a conventional, somewhat straight, laryngoscope.

An alternate embodiment of the laryngoscope 130 of the present invention can best be seen in FIG. 7, which is a diagrammatic side elevational view of an alternate embodiment of the present invention attached to a conventional, somewhat straight, laryngoscope, and as such, will be discussed with reference thereto.

A conventional, somewhat straight, laryngoscope blade 112 can be adapted to the advantages of the present invention by use of an adapter 166.

The adapter 166 replicates the present invention in that it comprises a portion of the first portion 138 of the blade, the second 140 and third 142 portions of the blade, and the screen 156 as a one-piece unit 168 that is attachable by attaching apparatus 170 to the conventional, somewhat straight, laryngoscope blade 112, and as a result thereof, adapts the operating surface 172 of the conventional, somewhat straight, laryngoscope blade 112, to the advantageous shape of the present invention.

It will be understood that each of the elements described above, or two or more together, may also find a useful application in other types of constructions differing from the types described above.

While the invention has been illustrated and described as embodied in a laryngoscope, however, it is not limited to the details shown, since it will be understood that various omissions, modifications, substitutions, and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of the invention.

The invention claimed is:

1. An improved laryngoscope of the type having a handle for grasping and a blade being rigid and extending from the handle for inserting into the mouth of a patient during use, wherein the improvement comprises:

the blade being so shaped for contacting, supporting, and displacement of the bottom of the mouth of the patient and not bearing on the lower teeth of the patient so as to avoid damage to the lower teeth of the patient during use and so as to allow the lower jaw of the patient to be opened during use and being so shaped for contacting the front of the lower jaw of the patient so as to allow the lower jaw of the patient to be thrust forwardly during use.

2. The improved laryngoscope as defined in claim 1, wherein the improvement further comprises the blade being serpentine-shaped.

3. The improved laryngoscope as defined in claim 1, wherein the improvement further comprises the blade having a first portion;

wherein said first portion of the blade has a proximal end;

wherein said proximal end of said first portion of the blade is disposed at the handle; wherein said first portion of the blade has a distal end; and wherein said first portion of the blade extends from said proximal end thereof to said distal end thereof in a concave configuration relative to, and for receiving but clearing and not being supported by, the lower teeth of the patient so as to avoid damage to the lower teeth of the patient during use.

4. The improved laryngoscope as defined in claim 3, wherein the improvement further comprises the blade having a second portion;

wherein said second portion of the blade has a proximal end;

wherein said proximal end of said second portion of the blade is coincident with said distal end of said first portion of the blade;

wherein said second portion of the blade has a distal end; and wherein said second portion of the blade extends from said proximal end thereof to said distal end thereof in a convex configuration relative to, and for contacting, the front of the lower jaw of the patient so as to allow the lower jaw of the patient to be thrust forwardly during use.

5. The improved laryngoscope as defined in claim 4, wherein the improvement further comprises said second portion of the blade transitioning smoothly upwardly from said first portion of the blade.

6. The improved laryngoscope as defined in claim 4, wherein the improvement further comprises the blade having a third portion;

wherein said third portion of the blade has a proximal end;

wherein said proximal end of said third portion of the blade is coincident with said distal end of said second portion of the blade;

wherein said third portion of the blade has a distal end; wherein said distal end of said third portion of the blade is for replicating a distal end of a blade of a conventional laryngoscope;

wherein said distal end of said third portion of the blade is for having a camera mounted thereon; and wherein said third portion of the blade extends from said proximal end thereof to said distal end thereof in a convex configuration relative to, and for contacting and being supported by, the bottom of the mouth of the patient so as to allow the lower jaw of the patient to be opened during use.

7. The improved laryngoscope as defined in claim 6, wherein the improvement further comprises said third portion of the blade transitioning smoothly outwardly from said second portion of the blade.

8. The improved laryngoscope as defined in claim 6, wherein the improvement further comprises said first portion of the blade having a radius of curvature;

wherein said third portion of the blade has a radius of curvature; and wherein said radius of curvature of said third portion of the blade is substantially greater than said radius of curvature of said first portion of the blade.

9. The improved laryngoscope as defined in claim 6, wherein the improvement further comprises a screen;

wherein said screen is pivotally mounted to said third portion of the blade;

wherein said screen extends conformingly to said second portion of the blade;

wherein said screen is dependable from said third portion of the blade; and wherein said screen is for blocking and confining the tongue of the patient to the side of the mouth so as to prevent the tongue from obstructing viewing during examination when said screen pivoted downwardly.

10. The improved laryngoscope as defined in claim 1, wherein the improvement further comprises means for distributing bearing pressure of the blade on the bottom of the mouth and the front of the lower jaw of the patient during use.

11. The improved laryngoscope as defined in claim 10, wherein the improvement further comprises said means including a resilient material.

12. The improved laryngoscope as defined in claim 11, wherein the improvement further comprises said resilient material being an elasomeric lining; and wherein said elasomeric lining extends along the blade.

13. The improved laryngoscope as defined in claim 11, wherein the improvement further comprises said resilient material being a balloon; and wherein said balloon receives the blade.

14. The improved laryngoscope as defined in claim 11, wherein the improvement further comprises said resilient material being an inflatable cushion; and wherein said inflatable cushion extends along the blade.

* * * * *